(12) United States Patent
Varona

(10) Patent No.: US 6,797,360 B2
(45) Date of Patent: Sep. 28, 2004

(54) NONWOVEN COMPOSITE WITH HIGH PRE-AND POST-WETTING PERMEABILITY

(75) Inventor: Eugenio Go Varona, Marietta, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 200 days.

(21) Appl. No.: 09/935,088

(22) Filed: Aug. 22, 2001

(65) Prior Publication Data

US 2003/0039817 A1 Feb. 27, 2003

(51) Int. Cl.[7] ............................. D06N 7/04; B32B 3/26; B32B 3/00; D21H 11/00; D21H 13/00; D04H 3/16; A61F 13/15; A61F 13/20
(52) U.S. Cl. ............... 428/152; 428/304.4; 428/311.11; 428/315.5; 442/401; 604/367; 604/380
(58) Field of Search ................... 428/304.4, 311.11, 428/315.5, 152; 442/401; 604/367, 380

(56) References Cited

U.S. PATENT DOCUMENTS

| | | | | |
|---|---|---|---|---|
| 3,670,731 A | * | 6/1972 | Harmon .................... 428/327 |
| 3,802,817 A | | 4/1974 | Matsuki et al. ............... 425/66 |
| 3,817,827 A | * | 6/1974 | Benz ......................... 428/152 |
| 3,855,046 A | | 12/1974 | Hansen et al. .............. 161/150 |
| 4,055,180 A | * | 10/1977 | Karami ....................... 604/368 |
| 4,100,324 A | | 7/1978 | Anderson et al. ........... 428/288 |
| 4,158,594 A | * | 6/1979 | Becker et al. ............... 428/153 |
| 4,215,682 A | | 8/1980 | Kubik et al. ........... 128/205.29 |
| 4,340,563 A | | 7/1982 | Appel et al. ................ 264/518 |
| 4,375,718 A | | 3/1983 | Wadsworth et al. ...... 29/592 E |
| 4,559,050 A | | 12/1985 | Iskra .......................... 604/368 |
| 4,592,815 A | | 6/1986 | Nakao ........................ 204/165 |
| 4,600,458 A | * | 7/1986 | Kramer et al. .............. 604/368 |
| 4,640,810 A | | 2/1987 | Laursen et al. ............. 264/518 |
| 4,655,757 A | | 4/1987 | McFarland et al. ......... 604/366 |
| 4,685,914 A | | 8/1987 | Holtman ..................... 604/368 |
| 4,793,280 A | | 12/1988 | Menard et al. ............... 118/44 |
| 4,818,464 A | | 4/1989 | Lau ............................ 264/510 |
| 4,874,659 A | | 10/1989 | Ando et al. ................. 428/221 |
| 5,100,397 A | | 3/1992 | Poccia et al. ............... 604/365 |
| 5,102,585 A | | 4/1992 | Pieper et al. ................. 264/37 |
| 5,156,902 A | | 10/1992 | Pieper et al. ............... 428/206 |
| 5,167,654 A | | 12/1992 | Yang ........................ 604/385.2 |
| 5,277,976 A | | 1/1994 | Hogle et al. ................ 428/397 |
| 5,279,854 A | | 1/1994 | Kendall et al. ............. 427/197 |
| 5,382,400 A | | 1/1995 | Pike et al. ................... 264/168 |
| 5,401,446 A | | 3/1995 | Tsai et al. ..................... 264/22 |
| 5,476,459 A | | 12/1995 | Yang ........................ 604/385.1 |
| 5,494,622 A | | 2/1996 | Heath et al. ................ 264/40.1 |
| 5,549,964 A | * | 8/1996 | Shohji et al. ............... 442/329 |
| 5,562,645 A | * | 10/1996 | Tanzer et al. ............... 604/368 |
| 5,601,542 A | * | 2/1997 | Melius et al. ............... 604/368 |
| 5,885,516 A | | 3/1999 | Christensen ................ 264/518 |
| 5,906,879 A | * | 5/1999 | Huntoon et al. ............ 428/152 |
| 6,129,717 A | | 10/2000 | Fujioka et al. .............. 604/368 |
| 6,139,912 A | * | 10/2000 | Onuschak et al. .......... 427/180 |
| 6,150,002 A | | 11/2000 | Varona ......................... 428/99 |
| 6,429,350 B1 | * | 8/2002 | Tanzer et al. ............... 604/368 |

FOREIGN PATENT DOCUMENTS

| | | | |
|---|---|---|---|
| EP | 1 053 729 | 11/2000 | ........... A61F/13/15 |
| WO | 98/33588 | 8/1998 | ........... B01J/20/02 |
| WO | 98/33644 | 8/1998 | ........... B32B/9/00 |
| WO | 99/22685 | 5/1999 | ........... A61F/13/15 |
| WO | 99/49905 | 10/1999 | ........... A61L/15/00 |
| WO | 00/26458 | 5/2000 | ........... D06B/5/08 |
| WO | 00/33780 | 6/2000 | ........... A61F/13/15 |
| WO | 00/33782 | 6/2000 | ........... A61F/13/15 |
| WO | 00/33783 | 6/2000 | ........... A61F/13/15 |
| WO | 00/38749 | 7/2000 | ........... A61L/15/60 |
| WO | 00/66057 | 11/2000 | ........... A61F/13/15 |
| WO | 00/66284 | 11/2000 | ............ B07C/7/02 |
| WO | 00/66824 | 11/2000 | ........... D04H/3/16 |

* cited by examiner

*Primary Examiner*—Elizabeth M. Cole
*Assistant Examiner*—Jeremy R. Pierce
(74) *Attorney, Agent, or Firm*—Nathan P. Hendon

(57) ABSTRACT

There is provided a new nonwoven material for personal care products made of fibers, binder in an amount between 1 and 6 weight percent and superabsorbent in an amount between 1 and 80 weight percent, where the superabsorbent is contained in micro-pockets in the nonwoven. These micro-pockets may be made by creping a nonwoven fabric, orienting fibers in the Z-direction, and by passing a relatively lofty nonwoven fabric between unheated thermal pattern bond and anvil rolls. These materials exhibit good permeability to liquid in the pre- and post-wetted conditions, thus avoiding gel blocking and other negative effects of superabsorbent swelling within a fabric. Such a fibrous material is useful in personal care products, like diapers, training pants, incontinence garments and feminine hygiene products.

15 Claims, No Drawings

NONWOVEN COMPOSITE WITH HIGH PRE-AND POST-WETTING PERMEABILITY

BACKGROUND OF THE INVENTION

The present invention concerns formed materials mainly for personal care products like diapers, training pants, swim wear, absorbent underpants, adult incontinence products and feminine hygiene products. This material may also be useful for other applications such as, for example, in bandages and wound dressings, nursing pads and in veterinary and mortuary applications.

Personal care articles usually have multiple layers of material of some sort to absorb liquids from the body. These layers may include natural fibers, synthetic fibers and superabsorbent particles in varying proportions. When liquid such as urine is deposited into a personal care product like a diaper, it goes through the uppermost layers, typically a liner against the body and a "surge" or "intake" layer designed to provide temporary liquid holding capacity. The product may also have a "distribution" layer designed to move liquid in the X and Y directions in order to utilize more of the absorbent core. After going through these upper layers, the urine enters the absorbent core portion of the product. The absorbent core permanently retains the liquid.

The functions of the layers mentioned above may each be performed by different layers or a layer may perform more than one function. The combination of more than one function in a single layer, however, generally results in a significant decrease in the performance of each of the functions.

Absorbent cores are typically composed of superabsorbent particles and/or pulp. A newer class of absorbents also uses a binder to improve wet stability and to ease converting into final products. Binders can be liquid adhesive or thermally activatable fibers typically present in amounts between 10 and 25 weight percent.

Superabsorbent particles absorb many times their weight in liquid and swell greatly as a result of being wetted. This swelling holds liquid within the product and so protects the wearer's skin, clothing and bedding, but may also block the further intake of liquid. This occurs because the swollen particles become so large as to close off fluid entrances to the structure, a phenomenon known in the art as "gel blocking".

Alternatively, an absorbent structure lacking superabsorbent and made of the traditional pulp and binder fiber can experience "wet collapse". This occurs as a result of saturation of the pulp and the subsequent inability to regenerate void space as fluid is added to the structure. The binder fibers, generally synthetic polymer fibers that are naturally hydrophobic, contribute to this problem since they interfere with the wicking performance of the structure due to their poor wettability. In addition, the constraints induced by the bonding of the binder fibers restrains expansion of the absorbent structure, further reducing void volume and decreasing the ultimate capacity of the material. If the structure were able to wick fluid away from the area of incipient wet collapse more efficiently, the phenomenon might be avoided completely.

A material which treads the fine line between wet collapse and gel blocking would be very desirable. Such a material would avoid the undesirable features of uncontrolled superabsorbent expansion while efficiently absorbing fluids. It would also avoid wet collapse by maintaining a sufficient pore structure, allowing liquid to continue moving through it. Such a material would exhibit high levels of multifunctional absorbent performance.

SUMMARY OF THE INVENTION

In response to the discussed difficulties and problems encountered in the prior art, a new structural composite comprising nonwoven fabric to which has been added superabsorbent has been developed. The superabsorbent is preferably in the form of particles (SAP). The SAP is placed in "micro-pockets" formed by various means like creping or the manual creation of depressions in the surface of the nonwoven using a pattern roll. The volume of the micro-pockets may be between 0.33 and 10 cubic millimeters. The SAP need not be uniformly placed in the web but may be located in a non-uniform manner across the width of the fabric. As a result of this construction, the nonwoven web remains permeable to liquids before and after wetting. When the web is wetted, the superabsorbent is free to swell without disrupting the fibrous network of the web since it is located in the discrete pockets. The web should have a permeability above 1500 darcys and preferably above 2000 darcys.

In this invention, at least one layer having a mixture of polymeric fibers, superabsorbent in an amount between 1 and 80 weight percent and binder in an amount between 1 and 6 weight percent is provided. More particularly, amounts of superabsorbent between 25 and 75 weight percent and still more particularly between 40 and 60 percent may be beneficial. Additional layers may be present as well and the inventive layer may be placed in a personal care product to act as a distribution and absorption layer. The inventive layer has good distribution properties, presumably due to the avoidance of gel blocking, capillary disruption and wet collapse, by virtue of the discrete placement of the superabsorbent. It is also possible to electrically treat the web of this invention to improve particle adherence.

These materials are suitable for use in personal care products like diapers, training pants, incontinence products, bandages, and sanitary napkins.

DEFINITIONS

As used herein the term "nonwoven fabric or web" means a web having a structure of individual fibers or threads which are interlaid, but not in an identifiable manner as in a knitted fabric. Nonwoven fabrics or webs have been formed from many processes such as for example, meltblowing processes, spunbonding processes, and bonded carded web processes. The basis weight of nonwoven fabrics is usually expressed in ounces of material per square yard (osy) or grams per square meter (gsm) and the fiber diameters useful are usually expressed in microns. (Note that to convert from osy to gsm, multiply osy by 33.91).

"Spunbonded fibers" refers to small diameter fibers that are formed by extruding molten thermoplastic material as filaments from a plurality of fine capillaries of a spinneret. Such a process is disclosed in, for example, U.S. Pat. No. 4,340,563 to Appel et al. and U.S. Pat. No. 3,802,817 to Matsuki et al. The fibers may also have shapes such as those described, for example, in U.S. Pat. No. 5,277,976 to Hogle et al. which describes fibers with unconventional shapes.

"Bonded carded web" refers to webs that are made from staple fibers which are sent through a combing or carding unit, which separates or breaks apart and aligns the staple fibers in the machine direction to form a generally machine direction-oriented fibrous nonwoven web. This material may be bonded together by methods that include point bonding, through air bonding, ultrasonic bonding, adhesive bonding, etc.

As used herein, the term "coform" means a process in which at least one meltblown diehead is arranged near a chute through which other materials are added to the web while it is forming. Such other materials may be pulp, superabsorbent particles, natural fibers (for example, rayon or cotton fibers) and/or synthetic fibers (for example, polypropylene or polyester) fibers, for example, where the fibers may be short cut of staple length. Coform processes are shown in commonly assigned U.S. Pat. No. 4,818,464 to Lau and U.S. Pat. No. 4,100,324 to Anderson et al. Webs produced by the coform process are generally referred to as coform materials.

"Airlaying" is a well-known process by which a fibrous nonwoven layer can be formed. In the airlaying process, bundles of small fibers having typical lengths ranging from about 3 to about 52 millimeters (mm) are separated and entrained in an air supply and then deposited onto a forming screen, usually with the assistance of a vacuum supply. The randomly deposited fibers then are bonded to one another using, for example, hot air to activate a binder component or a latex adhesive. Airlaying is taught in, for example, U.S. Pat. No. 4,640,810 to Laursen et al., and U.S. Pat. No. 5,885,516 to Christensen.

The term "creping" means a process for folding a web such that loops are created in the web structure. Such loops define an arch, semi-circle or similar configuration extending above the plane of the uncreped nonwoven web, and terminating at both ends in the nonwoven web. Examples of creped materials and methods may be found in U.S. Pat. No. 6,150,002 to Varona and PCT publication WO 00/33780 (U.S. application Ser. No. 09/209,044) to Varona et al. Crepe level (CL) is a measure of creping expressed as a percentage and is calculated as the speed of the creping drum surface (A) minus the speed of the windup reel for the creped web (B) divided by the speed of the creping drum surface (A), multiplied by 100, or: $CL=(A-B)/A*100$.

"Z-direction materials" refers to fabrics wherein the fibers are predominately oriented in the Z-direction during the formation of the fabric, as opposed to during a post-treatment step like creping. Examples of such materials and methods may be found in PCT publication WO 00/66057 and WO 00/66284, corresponding to U.S. application Ser. Nos. 09/538,744 and 09/537,564, respectively, and both commonly assigned.

The term "micro-pockets" means small pockets, in the order of a few cubic millimeters or less, formed in a nonwoven web. They must be sufficiently large to allow entry for and provide storage for superabsorbent particles.

As used herein "thermal point bonding" involves passing a fabric or web of fibers to be bonded between a heated calender roll and an anvil roll. The calender roll is usually, though not always, patterned in some way so that the entire fabric is not bonded across its entire surface, and the anvil roll is usually flat. As a result, various patterns for calender rolls have been developed for functional as well as aesthetic reasons. One example of a pattern has points and is the Hansen Pennings or "H&P" pattern with about a 30% bond area with about 200 bonds/square inch as taught in U.S. Pat. No. 3,855,046 to Hansen and Pennings. The H&P pattern has square point or pin bonding areas wherein each pin has a side dimension of 0.038 inches (0.965 mm), a spacing of 0.070 inches (1.778 mm) between pins, and a depth of bonding of 0.023 inches (0.584 mm). The resulting pattern has a bonded area of about 29.5%. Another typical point bonding pattern is the expanded Hansen Pennings or "EHP" bond pattern which produces a 15% bond area with a square pin having a side dimension of 0.037 inches (0.94 mm), a pin spacing of 0.097 inches (2.464 mm) and a depth of 0.039 inches (0.991 mm). Another typical point bonding pattern designated "714" has square pin bonding areas wherein each pin has a side dimension of 0.023 inches, a spacing of 0.062 inches (1.575 mm) between pins, and a depth of bonding of 0.033 inches (0.838 mm). The resulting pattern has a bonded area of about 15%. Yet another common pattern is the C-Star pattern which has a bond area of about 16.9%. The C-Star pattern has a cross-directional bar or "corduroy" design interrupted by shooting stars. Other common patterns include a diamond pattern with repeating and slightly offset diamonds with about a 16% bond area and a wire weave pattern looking as the name suggests, e.g. like a window screen, with about a 19% bond area. Typically, the percent bonding area varies from around 10% to around 30% of the area of the fabric laminate web. As in well known in the art, the spot bonding holds the laminate layers together as well as imparts integrity to each individual layer by bonding filaments and/or fibers within each layer.

As used herein, through-air bonding or "TAB" means a process of bonding a nonwoven bicomponent fiber web in which hot air is forced through the web. The temperature of the air is sufficient to melt one of the polymers of which the fibers are made. The air velocity is usually between 100 and 500 feet per minute and the dwell time may be as long as 6 seconds. The melting and resolidification of the polymer provides bonding. Through-air bonding (TAB) requires the melting of at least one component to accomplish bonding, so it is usually restricted to webs with two components like conjugate fibers or those which include an adhesive. In the through-air bonder, air having a temperature above the melting temperature of one component and below the melting temperature of another component is directed from a surrounding hood, through the web, and into a perforated drum supporting the web. Alternatively, the through-air bonder may be a flat arrangement wherein the air is directed vertically downward onto the web. The operating conditions of the two configurations are similar, the primary difference being the geometry of the web during bonding. The hot air melts the lower melting polymer component and thereby forms bonds between the filaments to integrate the web.

"Personal care product" means diapers, training pants, swim wear, absorbent underpants, adult incontinence products, bandages and feminine hygiene products. It may further encompass veterinary and mortuary products.

TEST METHODS AND MATERIALS

Basis Weight

A circular sample of 3 inches (7.6 cm) diameter is cut and weighed using a balance. Weight is recorded in grams. The weight is divided by the sample area. Five samples are measured and averaged.

Material Caliper (Thickness)

The caliper of a material is a measure of thickness and is measured at 0.05 psi (3.5 $g/cm^2$) with a STARRET® bulk tester, in units of millimeters. Samples are cut into 4 inch by 4 inch (10.2 cm by 10.2 cm) squares and five samples are tested and the results averaged.

Density

The density of the materials is calculated by dividing the weight per unit area of a sample in grams per square meter (gsm) by the material caliper in millimeters (mm). The caliper should be measured at 0.05 psi (3.5 $g/cm^2$) as mentioned above. The result is multiplied by 0.001 to convert the value to grams per cubic centimeter (g/cc). A total of five samples would be evaluated and averaged for the density values.

Permeability

Permeability (k, in cm$^2$) may be calculated and represents the resistance to flow of a liquid by a material. A liquid of known viscosity ($\eta$, in Pascal-sec) is forced through the material of given thickness (t, in cm) at a constant flow rate (v, in cm/sec) and the resistance to flow, measured as a pressure drop ($\Delta P$, in Pascal's) is monitored. Permeability is calculated using Darcy's flow equation:

$$k=vt\eta/\Delta P$$

Note that 1 darcy=9.87×10$^{-9}$ cm$^2$
In a test for permeability, typical parameters are: a velocity of 20 cm/sec, a sample thickness of 20–50 mils and a test liquid having a viscosity of about 6 Pascal-sec.

DETAILED DESCRIPTION OF THE INVENTION

This invention nonwoven web having superabsorbent contained within micro-pockets. This web has a high permeability and maintains high permeability to liquid flow even after being wetted. A permeability above 1500 darcys, and preferably above 2000 darcys is considered "high".

The nonwoven web of this invention may be made from a number of processes, including airlaying, spunbonding, bonding and carding, meltblowing and coforming. The material may be creped after formation, given Z-direction fiber orientation during formation, or may be a relatively flat nonwoven structure into which micro-pockets are depressed. Additional layers may be added to the structure and it may be included in personal care products.

The volume in the micro-pockets may be calculated relatively easily and is dependent upon the method of making the pockets. One embodiment of this invention is a creped, pre-bonded spunbond fabric. This is typically thermally bonded as it is produced with an EHP or other pattern in with either a square or diamond layout of the bond points (other layouts may be used but the calculations must be modified). As the fabric is creped, bond points will adhere to the creping drum as it is processed, causing the fabric to increase its Z-directional dimension and decrease or shorten in the X-direction. This results the creation of the "micro-pockets" useful in this invention for holding superabsorbent, which, in the case of creping, are perhaps more readily envisioned as bulges of fiber between the bond points with space created between the fibers to accommodate the SAP. A typical EHP pattern has bond points spaced about 2.464 mm apart (see definition above) in a square or diamond pattern. Upon creping, the distance (a) between bond points decreases approximately by the crepe level (CL) expressed as a percentage and the height of the fabric increases approximately by the crepe level, yielding an area and volume encompassed by any four bond points of:

Area=((100−CL)*a$^2$)/100

Volume for square pattern=area (a*CL)/200

Volume for diamond pattern=area (2$^{0.5}$*a/2*CL)/200

It should be noted that the minor differences between the square and diamond pattern volumes are due to the orientation of the web when it undergoes creping. A square pattern bonded fabric enters the creping apparatus with two edges of a box formed by four bond points in the machine direction (MD) and two in the cross direction (CD). A diamond pattern bonded fabric does not have such an orientation and instead is oriented with the edges of a box formed by four bond points approximately 45 degrees away from either the cross or machine directions. Other bonding patterns may of course be used. In such cases, the correct area and volume must be calculated. This may be done by those skilled in the art and may be aided by standard references such as for example, the CRC Standard Mathematical Tables from the CRC Press of Cleveland, Ohio.

Creping the webs contemplated for the practice of this invention results in volumes of between about 0.33 to 10 cubic mm, more particularly between 0.33 and 5 cubic mm, more particularly between 0.5 and 1 cubic mm and still more particularly between 0.5 and 2 cubic mm.

As one example of this invention, a nonwoven web may be creped at a level of about 40 percent, and tumbled in a drum with superabsorbent particles to make an addition rate of about 50 weight percent. Such an addition of particles would be in all of the micro-pockets in the fabric, i.e., uniformly, assuming the micro-pockets were distributed uniformly. Alternatively, a length of creped fabric could be unwound around a roller or bar in order to open the folds of the creped fabric. As the fabric passes over the roller, superabsorbent particles could be added in a uniform or non-uniform pattern to these folds. Such embodiments are intended to be within the scope of this invention.

Another method of making the web of this invention is to begin with a relatively flat web and pass it between a pattern and anvil roll to create depressions in the fabric. A lofty fabric is preferred for this embodiment since it will allow the fabric to have sufficient depth to provide adequate micro-pockets. Lofty fabrics are preferably bonded in a through-air bonder rather than by thermal point bonding because thermal point bonding tends to compact the fabric as it passes between the rollers. A bicomponent crimped fabric, like, for example, the fabric of U.S. Pat. No. 5,382,400 to Pike, that may be through-air bonded, should work well in the practice of this invention. After formation and bonding, the depressions may be created in the fabric. This may be done, for example, by using unheated thermal point bonding and flat anvil rolls. The unheated pattern roll would not use a pattern that would pass fully through the web but would only depress the web in pre-selected areas. The pattern may be uniform or non-uniform, providing depressions to only certain areas of the web or providing a changing density of depressions to the web. Patterns which may be used for the creation of depression are greatly varied, including those mentioned above for thermal point bonding, like the EHP, H&P and 714 patterns. After the formation of the depressions, superabsorbent may be deposited on the web to fill all or some of the depressions to the degree desired.

In the case of a pattern and anvil roll used to create depressions in a fabric, the calculation to determine the size of the micro-pockets will be dependent upon the size of the pins used in the pattern roll and the depth of penetration of the pins into the fabric. The H&P pattern, if fully inserted into a fabric, produces a micro-pocket with a volume of about 0.544 cubic mm and the EHP a volume of about 0.876 cubic mm, for example.

If the fabric to which the superabsorbent is added is creped, the superabsorbent should remain in place in micro-pockets formed in the folds of the fabric when the fabric resumes its normal position. If the fabric is relatively flat and provided with depressions, an adhesive may be needed to hold the superabsorbent in place. Alternatively, electrostatic charge may be used to encourage the superabsorbent to remain in the depressions by means of differing electrical polarities or potentials.

Electrostatic charging of webs is accomplished by electret treatment which draws particles toward the fabric by virtue of their electrical charge. Electret treatment can be carried out by a number of different techniques. One technique is described in U.S. Pat. No. 5,401,446 to Tsai et al. assigned to the University of Tennessee Research Corporation. Tsai describes a process whereby a web or film is sequentially subjected to a series of electric fields such that adjacent electric fields have substantially opposite polarities with respect to each other. Thus, one side of the web or film is initially subjected to a positive charge while the other side of the web or film is initially subjected to a negative charge. Then, the first side of the web or film is subjected to a negative charge and the other side of the web or film is subjected to a positive charge. Such webs are produced with a relatively high charge density without an attendant surface static electrical charge. The process may be carried out by passing the web through a plurality of dispersed non-arcing electric fields which may be varied over a range depending on the charge desired in the web. The web may be charged at a range of about 1 kVDC/cm to 12 kVDC/cm or more particularly 4 kVDC/cm to 10 kVDC/cm and still more particularly 7 kVDC/cm to about 8 kVDC/cm. Other methods of electret treatment are known in the art such as that described in U.S. Pat. No. 4,215,682 to Kubik et al, U.S. Pat. No. 4,375,718 to Wadsworth, U.S. Pat. No. 4,592,815 to Nakao and U.S. Pat. No. 4,874,659 to Ando.

The fabric used in the practice of this invention may have natural fibers, though webs of synthetic polymer fibers are preferred. An effective amount of binder, typically from 1 to 6 weight percent (based on the web weight before addition of superabsorbent), may be present to help provide mechanical integrity by binding the fibers and particles together. The binder may more particularly be between 1 and 5 percent and still more particularly between 1 and 4 percent. As much as 80 percent by weight of the web may be added as superabsorbent. A more particular range for the superabsorbent is between 25 and 75 weight percent and still more particularly between 40 and 60 weight percent.

Superabsorbents that are useful in the present inventions can be chosen from classes based on chemical structure as well as physical form. These include superabsorbents with low gel strength, high gel strength, surface cross-linked superabsorbents, uniformly cross-linked superabsorbents, or superabsorbents with varied cross-link density throughout the structure. Superabsorbents may be based on chemistries that include poly(acrylic acid), poly(iso-butylene-co-maleic anhydride), poly(ethylene oxide), carboxy-methyl cellulose, poly(vinyl pyrrollidone), and poly(-vinyl alcohol). The superabsorbents may range in swelling rate from slow to fast. The superabsorbents may be in the form of foams, macroporous or microporous particles or fibers, particles or fibers with fibrous or particulate coatings or morphology. The superabsorbents may be in the shape of ribbons, particles, fibers, sheets or films. Superabsorbents in the form of particles are preferred for the practice of this invention. Superabsorbents may be in various length and diameter sizes and distributions. The superabsorbents may be in various degrees of neutralization. Counter-ions are typically Li, Na, K, Ca.

An exemplary superabsorbent was obtained from Stockhausen, Inc and is designated FAVOR® SXM 880. Another example of these types of superabsorbents may be obtained from the Dow Chemical Company under the name DRYTECH® 2035. An example of fibrous superabsorbents may be obtained from Camelot Technologies, Ltd., of High River, Alberta, Canada and is designated FIBERDRI® 1241. Another Example included in these types of superabsorbents is obtained from Chemtall Inc. or Riceboro, Ga., and is designated FLOSORB 60 LADY®, also known as LADYS-ORB 60®. Additional types of superabsorbents not listed here which are commonly available and known to those skilled in the art can also be useful in the present inventions.

Binders typically used in these structures help provide mechanical integrity and stabilization. Binders include fiber, liquid or other binder means that may be thermally activated. Preferred fibers for inclusion are those having a relative melting point such as polyolefin fibers. Lower melting point polymers provide the ability to bond the fabric together at fiber cross-over points upon the application of heat. In addition, fibers having a lower melting polymer, like conjugate and biconstituent fibers are suitable for practice of this invention. Fibers having a lower melting polymer are generally referred to as "fusible fibers". By "lower melting polymers" what is meant are those having a glass transition temperature less than about 175° C. It should be noted that the texture of the absorbent web can be modified from soft to stiff through selection of the fusion and quenching behavior of the polymer. Exemplary binder fibers include conjugate fibers of polyolefins, polyamides and polyesters. Three suitable binder fibers are sheath core conjugate fibers available from KoSa Inc. (Charlotte, N.C.) under the designation T-255 and T-256, both with a polyolefin sheath, or T-254, which has a low melt co-polyester sheath. Many suitable binder fibers are known to those skilled in the art, and are available by many manufacturers such as Chisso and Fibervisions LLC of Wilmington, Del. A suitable liquid binder is KYMENE® 557LX available from Hercules Inc. of Wilmington, Del. Other suitable liquid binders include ethylene vinyl acetate emulsion polymers sold by National Starch and Chemical Company (Bridgewater, N.J.) under the tradename DUR-O-SET® ELITE® series (including ELITE® 33 and ELITE® 22). Other suitable binders are sold by Air Products Polymers and Chemicals under the name AIRFLEX®.

Synthetic fibers include those made from polyolefins, polyamides, polyesters, rayon, acrylics, superabsorbents, TENCEL® regenerated cellulose and any other suitable synthetic fibers known to those skilled in the art. Synthetic fibers may also include kosmotropes for product degradation.

Many polyolefins are available for fiber production, for example polyethylenes such as Dow Chemical's ASPUN® 6811A liner low density polyethylene, 2553 LLDPE and 25355 and 12350 high density polyethylene are such suitable polymers. The polyethylenes have melt flow rates, respectively, of about 26, 40, 25 and 12. Fiber forming polypropylenes include Exxon Chemical Company's ESCORENE® PD 3445 polypropylene and Montell Chemical Co.'s PF304. Many other polyolefins are also available.

Natural fibers include wool, cotton, flax, hemp and wood pulp. Wood pulps include standard softwood fluffing grade such as NB-416 (Weyerhaeuser Corporation, Tacoma, Wash.) and CR-1654 (US Alliance Pulp Mills, Coosa, Ala.). Pulp may be modified in order to enhance the inherent characteristics of the fibers and their processability. Curl may be imparted to the fibers by methods including chemical treatment or mechanical twisting. Curl is typically imparted before crosslinking or stiffening. Pulps may be stiffened by the use of crosslinking agents such as formaldehyde or its derivatives, glutaraldehyde, epichlorohydrin, methylolated compounds such as urea or urea derivatives, dialdehydes such as maleic anhydride, non-methylolated urea derivatives, citric acid or other polycarboxylic acids. Some of these agents are less preferable than others due to environmental and health concerns. Pulp may also be stiffened by the use of heat or caustic treatments such as mercerization. Examples of these types of fibers include NHB416 which is a chemically crosslinked southern softwood pulp fibers which enhances wet modulus, available from the Weyerhaeuser Corporation of Tacoma, Wash. Other useful pulps are debonded pulp (NF405) also from Weyerhaeuser. HPZ3 from Buckeye Technologies, Inc of Memphis, Tenn., has a chemical treatment that sets in a curl and twist, in addition to imparting added dry and wet stiffness and resilience to the fiber. Another suitable pulp is Buckeye HPF2 pulp and still another is IP SUPERSOFT® from International Paper Corporation. Suitable rayon fibers are 1.5 denier Merge 18453 fibers from Tencel Incorporated of Axis, Ala.

Examples and Comparative Examples, follow:

EXAMPLE 1

A 0.4 Osy (13.6 gsm) polypropylene web composed of 3.5 denier fibers was made according to the spunbonding process, bonded with a diamond EHP pattern end creped 25 percent producing micro-pockets with a volume of 0.992, cubic mm each. This material had a basis weight after creping of 0.5 osy (17 gsm) and was tumbled to add superabsorbent particles up to a 36 percent loading by weight on a dry basis. The permeability of the dry, (unswollen) composite web was 2000 darcys, according to the test method above. The fluid used for the testing was a mineral oil having a viscosity of 6 Pascal/sec and sold under the trade name PENETECK®. A sample of the composite web was placed in a large volum of 0.9 weight percent saline solution for sufficient time (approx. 20 minutes) to swell approximately to equilibrium. The swollen web was removed from the saline solution bath, dried on its surface, and tested for permeability in the same manner as the unswollen web. The permeability of the fully swollen composite web was 2060 darcys.

EXAMPLE 2

A 0.4 osy (13.6 gsm) polypropylene web composed of 3.5 denier fibers was made according to the spunbonding process, bonded with a diamond EHP pattern and creped 35 percent to produce micro-pockets with a volume of 1.2 cubic mm each. This material had a basis weight after creping of 0.54 osy (18.3 gsm) and was tumbled to add superabsorbent particles up to a 45 percent loading by weight on a dry basis. The permeability of the dry, (unswollen) composite web was 2100 darcys, according to the test method above. The permeability of the fully swollen composite web was 2133 darcys.

Comparative Example 1

A 0.4 osy (13.6 gsm) polypropylene web composed of 3.5 denier fibers was made according to the spunbonding process, bonded with an EHP pattern. No superabsorbent particles were added to the web. The permeability of the dry web as 450 darcys.

Comparative Example 2

A composite composed of 35 weight percent superabsorbent and 75 weight percent pulp was made by the airlaying process. The composite was compressed to an initial density of 0.2 g/cc. The dry permeability was 10 darcys and the swollen permeability was 16 darcys.

As can be seen above, the Examples had high permeabilities and maintained their permeabilities well upon being wetted.

As will be appreciated by those skilled in the art, changes and variations to the invention are considered to be within the ability of those skilled in the art. Examples of such changes and variations are contained in the patents identified above, each of which is incorporated herein by reference in its entirety to the extent consistent with this specification. Such changes and variations are intended by the inventors to be within the scope of the invention.

What is claimed is:

1. A single-layer lofty nonwoven web comprising fibers, binder, and superabsorbent, wherein said web is creped to produce micro-pockets and wherein said superabsorbent is placed and held in said micro-pockets and where said micro-pockets are between about 0.33 and about 10 cubic millimeters in volume.

2. The web of claim 1 wherein said nonwoven web is electret treated prior to addition of said superabsorbent.

3. The web of claim 1 having a permeability above 1500 darcys.

4. The web of claim 1 having a permeability above 2000 darcys.

5. A single-layer nonwoven material for personal care products comprising a mixture of fibers, binder, and superabsorbent, where the binder is present in an amount between 1 and 6 weight percent based on a web weight before the addition of the superabsorbent and where the superabsorbent is added in an amount between 1 and 80 weight percent based on the weight of the web, wherein said superabsorbent is contained and held in micro-pockets is said nonwoven formed by creping and wherein said micro-pockets are between about 0.33 to about 10 cubic millimeters in volume.

6. The material of claim 5 wherein said superabsorbent concentration in said nonwoven is between 25 and 75 weight percent.

7. The material of claim 5 wherein said superabsorbent concentration in said nonwoven is between 40 and 60 weight percent.

8. The material of claim 5 wherein said micro-pockets are between 0.5 and 5 cubic millimeters.

9. A diaper comprising the material of claim 5.

10. A training pant comprising the material of claim 5.

11. An incontinence product comprising the material of claim 5.

12. A bandage comprising the material of claim 5.

13. A sanitary napkin comprising the material of claim 5.

14. The material of claim 5 wherein said nonwoven web is electret treated prior to addition of said superabsorbent.

15. A single-layer nonwoven material, for personal care products comprising a mixture of spunbonded fibers, binder, and superabsorbent, where the binder is present in an amount between 1 and 6 weight percent based on a web weight before the addition of the superabsorbent and the superabsorbent is added in an amount between 1 and 80 weight percent based on the weight of the web, wherein said superabsorbent is contained and held in micro-pockets in said nonwoven formed by creping and wherein said micro-pockets are between about 0.33 to about 10 cubic millimeters in volume.

* * * * *